United States Patent [19]
White

[11] Patent Number: 5,170,501
[45] Date of Patent: Dec. 15, 1992

[54] WELDING MASK TO PREVENT ORANGE FLARE AND METHOD OF WELDING

[76] Inventor: R. Kent White, 17167 Salmon Mine Rd., Nevada City, Calif. 95959

[21] Appl. No.: 706,544

[22] Filed: May 23, 1991

Related U.S. Application Data

[63] Continuation of Ser. No. 518,445, May 4, 1990, abandoned.

[51] Int. Cl.$^5$ .............................................. A61F 9/06
[52] U.S. Cl. ........................................... 2/8; 359/361; 359/885; 359/355
[58] Field of Search ......................... 2/8, 432; 219/147; 350/311, 1.1, 1.6, 318; 359/355, 361, 350, 885

[56] References Cited

U.S. PATENT DOCUMENTS

| | | | |
|---|---|---|---|
| 4,330,177 | 5/1982 | Miller | 350/311 |
| 4,707,860 | 11/1987 | Holstrom | 2/8 |
| 4,730,902 | 3/1988 | Suzuki et al. | 350/311 |
| 4,755,012 | 7/1988 | Kojima | 350/1.1 |

OTHER PUBLICATIONS

Brochure published by Schott Glass Technologies Inc. of Duryea, Pennsylvania, entitled "Glass for CRT and Other Display Applications." (May 1988).
Brochure entitled "GVK-545 Monochromatic CRT Display Filter" printed by Hoya Optics, Inc. of Fremont, CA.

*Primary Examiner*—Peter Nerbun
*Attorney, Agent, or Firm*—Flehr, Hohbach, Test, Albritton & Herbert

[57] ABSTRACT

An improved welding mask glass to prevent orange flare is provided by utilizing as the glass in the lens a narrow bandpass green glass sold under Model S-8008N from Schott Glass Technologies, Inc., of Duryea, Pennsylvania. The transmission characteristic of the glass is a sharp cutoff from a peak of 544 nanometers toward the infrared which rejects objectionable "orange flares."

5 Claims, 2 Drawing Sheets

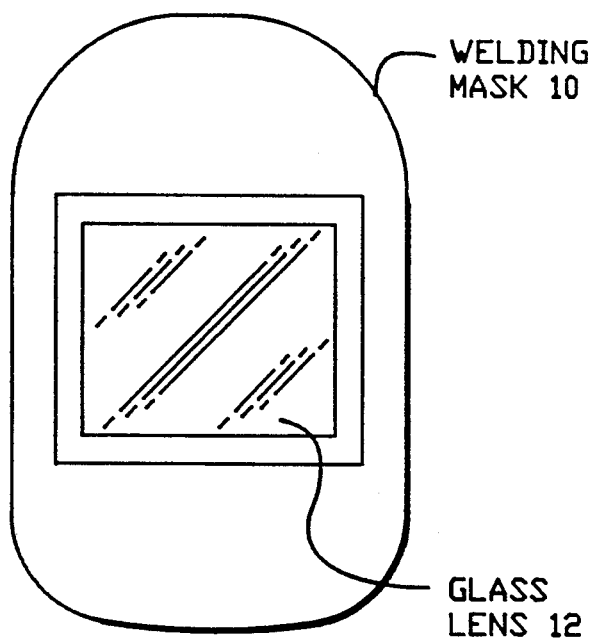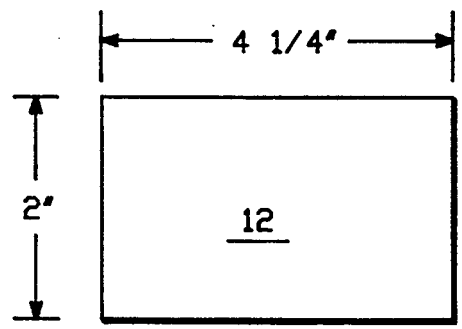
FIG.-1  FIG.-2
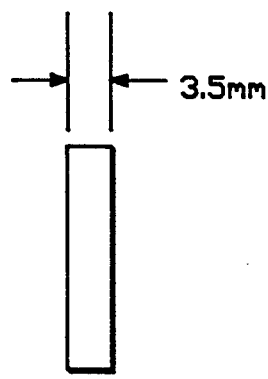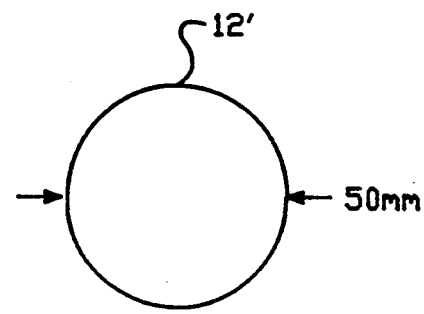
FIG.-3  FIG.-4

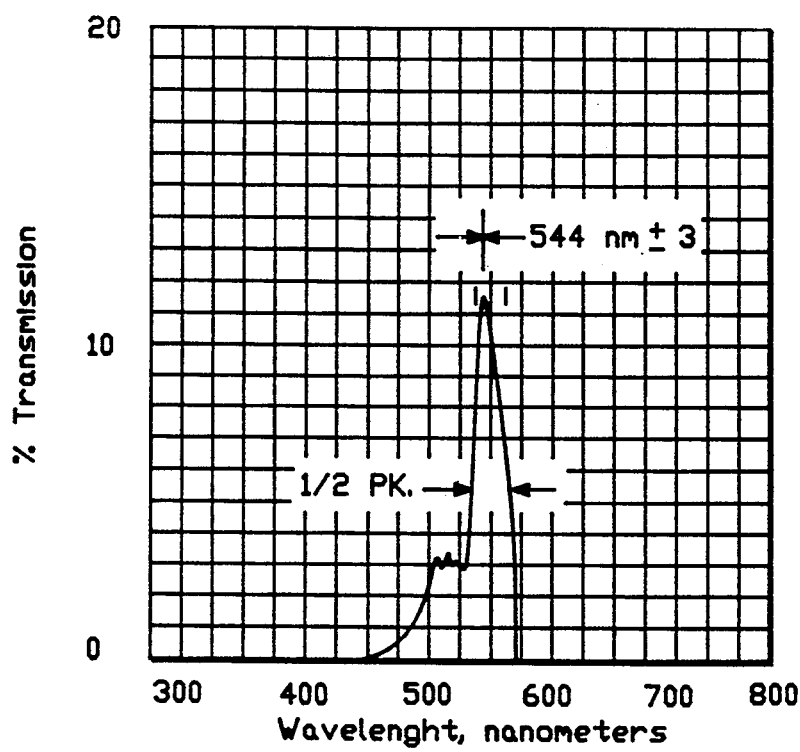
FIG.—5
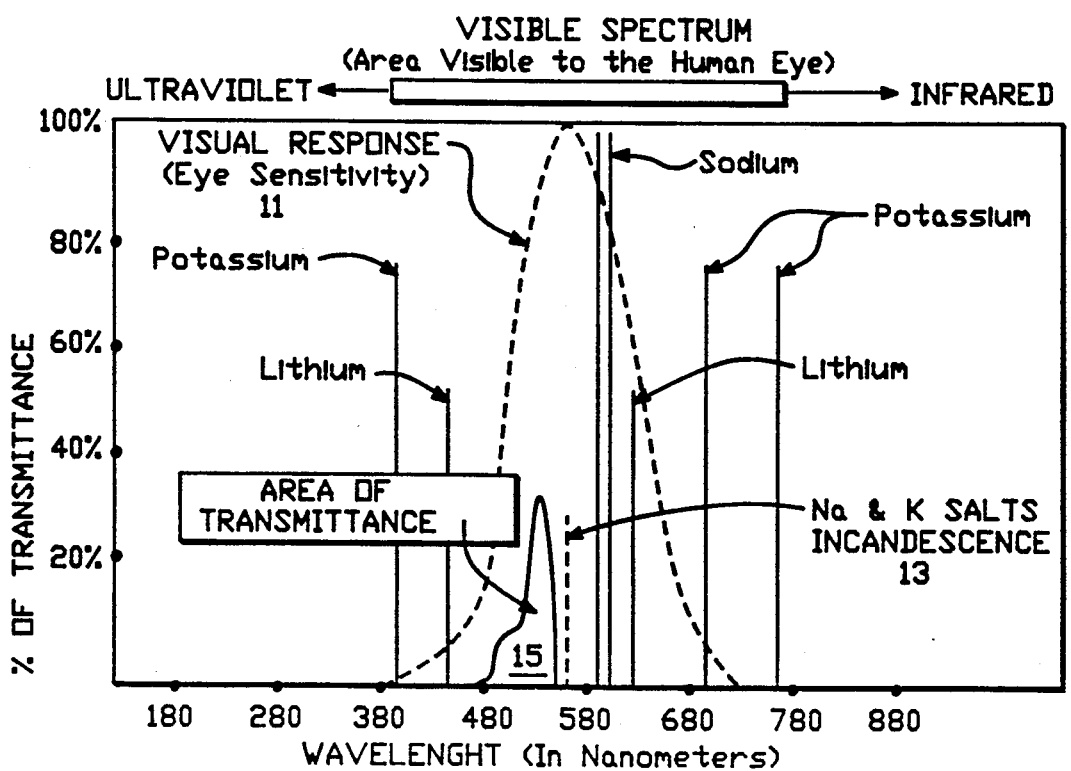
FIG.—6

WELDING MASK TO PREVENT ORANGE FLARE AND METHOD OF WELDING

This is a continuation of application Ser. No. 07/518,445 filed May 4, 1990, now abandoned.

BACKGROUND OF THE INVENTION

The present invention is directed to a welding mask to prevent orange flare and method of welding and more specifically to the use of a particular type of glass to provide adequate optical protection to the eyes during welding.

In high temperature welding using an oxygen-type fuel (such as natural gas, propane, acetylene and hydrogen) in brazing, and where fluxes are used, several flashes or wavelengths of light will be present which will normally irritate or damage the human eye unless eye protection is provided. In addition to visible wavelengths, it is also necessary to protect against the infrared and ultraviolet portions of the light spectrum. And this is of course the reason for the use of a welding mask or goggles.

However, existing protective lenses have not been perfected in that some eye damage and eye strain to welders still result. For example, the strong yellow-orange flare given off by many welding fluxes (which is believed due to the presence of sodium and potassium salts) at the present time is not effectively filtered and causes severe eye strain and headaches at a minimum and perhaps even vision loss. And, of course, the long term effect of this eye strain may be glaucoma.

OBJECT AND SUMMARY OF INVENTION

It is therefore a general object of the present invention to provide an improved welding mask and a method of welding.

In accordance with the above object, there is provided a welding mask or goggle having a filter glass lens for protection of the human eye (where the eyes have a predetermined visual response frequency characteristic) in a welding environment where light flashes of high intensity may occur within the visual characteristic. The filter glass lens comprises a filter glass shaped for use as the lens, having a narrow bandpass, green color, and is sold under one of Model Nos. S-8008N or S-8006W from Schott Glass Technologies, Inc., of Duryea, Pa., and Model No. GVK-545 from Hoya Optics of Fremont, Calif.

BRIEF DESCRIPTION OF DRAWINGS

FIG. 1 is an elevation view of a welding mask incorporating the glass lens of the present invention.

FIG. 2 is an enlarged elevation view of the glass lens faceplate of FIG. 1.

FIG. 3 is a side view of FIG. 2.

FIG. 4 is an alternative embodiment of a glass lens for welding for use in goggles.

FIG. 5 is the optical transmission characteristic of the preferred glass of the present invention.

FIG. 6 shows again the transmission characteristic of FIG. 5 overlaid with the visual response of the human eye and various wavelengths of light occurring during typical flux welding.

DETAILED DESCRIPTION OF PREFERRED EMBODIMENT

FIG. 1 illustrates the use of the present invention in a welding mask 10 for protection of human eyes in a welding environment where light flashes of high intensity may occur within the visual characteristic or response of the eye.

FIG. 6 shows this visual response curve 11.

Now referring back to FIG. 1, included in welding mask 10 is a rectangular glass lens 12 consisting of a single plate of filter glass which filters out harmful wavelengths of light both visible and infrared and ultraviolet to protect the welder's eyes. As discussed above, this includes an orange flare which occurs in high temperature welding, typically using fluxes. It also might occur in silver brazing and in gas welding with aluminum. And as discussed above, this so-called orange flare has not been practically eliminated from prior welding mask lens.

The rectangular lens 12, which is typically a United States standard, is illustrated in FIG. 2 and has dimensions typically of $2 \times 4\frac{1}{4}''$. In the preferred embodiment the specific thickness of the glass has been chosen at 3.5 mm, as illustrated in FIG. 3. This provides a thin enough glass to easily fit into the welding mask 10. Also, as will be discussed below, the type of glass used still provides a darkness or visible transmission range suitable for high temperature welding. These darknesses are classified as "shades" and the present glass lens is shade 4. Of course with a different type of glass, as will be discussed with an alternative embodiment of the present invention, a greater thickness dimension can be used to provide the desired darkness.

FIG. 4 illustrates a European type of glass lens 12' which is circular and has a standard diameter of 50 mm. This would be used in a goggle type of welding mask.

Referring now to FIG. 6, in high temperature flux welding (and other types of welding such as aluminum brazing, etc.) there are several wavelengths of light or "flashes" which occur in the welding environment and which may be, because of their intensity, damaging to the human eye. These may typically be due to the presence of sodium and potassium salts and also lithium; thus, the vertical lines labelled with those elements illustrate the undesired wavelengths which must be rejected by the filter lens of the welding mask. The area of transmittance of the filter glass lens 12 provided by the present invention is shown at 15 and designated "area of transmittance." It is shown in greater detail in FIG. 5. Referring to both figures, this area of transmittance clearly avoids the major potassium, lithium, sodium wavelengths, and in addition, a wavelength indicated at 13 due to the incandescence of sodium and potassium salts. While other filter glass lens for welding have perhaps filtered some of the more extreme potassium and sodium wavelengths, this wavelength at 13 is believed to have been the principal cause of the orange flare which has up to the present time been harmful to the eyes of welders. The transmittance curve of the glass utilized for the welding lens of the present invention avoids this wavelength by providing, as more clearly illustrated in FIG. 5, a narrow bandpass characteristic which is centered at 544 nanometers ±3 and having a sharp cutoff toward the infrared. In fact, as illustrated in FIG. 5, the bandpass of the transmission characteristic at one-half peak is less than 28 nanometers. The peak transmission is 11.5%. This is accomplished with a thickness of 3.5 mm.

The specific glass to provide the transmission characteristic of FIG. 5 is a green glass available from Schott Glass Technologies, Inc., of Duryea, Pa., under Model No. S-8008N. The transmission curve of the glass lens 12 is narrow bandpass in that it rejects all wavelengths toward the ultraviolet substantially below approximately 465 nanometers and due to the sharp cutoff, wavelengths above approximately 570 nanometers. And this upper cutoff is of critical importance with relation to the wavelength 13 (see FIG. 6) for the incandescence of sodium and potassium salts.

In addition to rejecting the other "virtual forest of wavelengths," of course, the filter glass of the present invention also provides infrared and ultraviolet protection as is apparent from its rejection characteristic. This is believed due to the inclusion of one of the materials in the filter glass, the rare-earth metal "didymium." This rare-earth metal is composed of two elements, neodymium (Nd) and praseodymium (Pr).

Finally, another major component of the glass is chromium oxide.

Thus, the glass filter lens of the present invention protects both the visual response frequency characteristic 11 of the human eye, as illustrated in FIG. 6, and also the damaging wavelengths in the infrared and ultraviolet regions of this light spectrum.

It is believed that while the above Model S-8008N is ideal, another model, No. S-8006W (also manufactured by Schott Glass Technologies) may be suitable. The only difference between the two glasses is that the "W" type has a peak transmission of 15% rather than 11.5% at a reference thickness of 7 mm. Thus, this type of glass is usable although its thickness and greater transmission make it less desirable than the "N" type. Yet another suitable glass is Model No. GVK-545 from Hoya Optics of Fremont, Calif.

Both of the glasses from Schott Technologies are commercially sold at the present time for use as cathode ray tube faceplates as enhancement filters to improve the contrast of video displays. Other models of glass from Schott in roughly the same glass family, such as the S-8005 and S-8006, are not suitable since their peaks, while occurring at 544 nanometers, do not have a sharp enough cutoff to reject the wavelength 13. Also, their transmission bandwidths may encompass the other sodium and lithium spikes toward the infrared. Thus, the transmission characteristic of the glass filter lens of the present invention is very critical when used in a welding mask or goggle or in fact, when used in the welding process.

In addition to providing a novel and improved glass lens in a welding mask, the present invention also improves the welding process where it makes possible high temperature flux welding without the attendant eye damage that has normally occurred.

It is also believed that a single unitary glass lens is ideal, as opposed to laminates or even the use of non-glass type filters. In the case of the use of non-glass filters, because of the heat encountered in the welding environment these are not suitable. Also, laminates are bulky, heavy and not so effective. Thus, the single unitary glass lens of the above type is believed to be unique and ideal for use in the welding process.

In preparing the glass for use in a welding mask or goggle, it of course must be shaped to the proper dimension, such as illustrated in FIGS. 2 and 4, to meet the European or American standards. In addition, the glass should be highly polished to eliminate stress risers and thus meet the impact requirements of the standards organizations such as ANSI.

The following are the various optical and physical properties of the Model S-8008N glass: refractive index 1.537, density 2.73, thermal expansion coefficient $85 \times 10^{-7}$, working point 1010, softening point 719, annealing point 533, transformation temperature 520, strain point 503. Transmission characteristics have already been discussed.

Finally, the typically green color characteristic has chromaticity co-ordinates of $x=0.2601$, $y=0.6965$ and $Y=3.3$.

The "W" type glass has the following characteristics: refractive index 1.539, strain point 464, transformation temperature 478, and thermal expansion co-efficient $94 \times 10^{-7}$.

The Hoya Model No. GVK-545 has peak at 545 nanometers with a similar narrow bandpass and sharp cutoff and the same thickness and peak transmission as the S-8008N glass. It is also "rich" in didymium for ultraviolet and infrared protection.

Thus, in summary, an improved glass lens has been provided for high temperature welding.

What is claimed is:

1. In a welding mask or goggle having a filter glass lens for protection of human eyes, said eyes having a predetermined visual response frequency characteristic, in a welding environment where light flashes of high intensity may occur within said visual characteristic, said filter glass lens comprising:
   a one-piece filter glass shaped for use as a said lens having a narrow bandpass to reject substantially all the ultraviolet wavelengths below 465 nanometers and substantially all infrared wavelengths above 570 nanometers with a transmission peak centered at a substantially 544 nanometer wavelength and having a sharp cutoff toward the infrared of substantially 570 nanometers and having substantial transmittance above 525 nanometers to provide an area of transmittance to the human eye between 525 and 570 nanometers.

2. In a welding mask or goggle as in claim 1 where said bandpass width at half of said peak is less than 28 nanometers.

3. In a welding mask or goggle as in claim 1 wherein said glass includes chromium dioxide.

4. In a welding mask or goggle as in claim 1 wherein said sharp cutoff filters the incandescence of sodium or potassium salts which may be present in the welding environment.

5. In a welding mask or goggle as in claim 1 wherein said glass has a peak transmittance of less than 15%.

* * * * *